United States Patent [19]
Bender et al.

[11] Patent Number: 5,571,921
[45] Date of Patent: Nov. 5, 1996

[54] SUBSTITUTED (2-OXO-1-BENZIMIDAZOLINYL)-PEPERIDINES, PROCESS FOR THEIR PREPARATION, AND USE AS ANTI-RETROVIRAL AGENTS

[75] Inventors: Wolfgang Bender; Dieter Häbich, both of Wuppertal; Siegfried Raddatz, Köln; Wolfgang Röben, Bergisch Gladbach; Hanno Wild; Jutta Hansen, both of Wuppertal; Arnold Paessens, Haan, all of Germany

[73] Assignee: Bayer Aktiengesellschaft, Leverkusen, Germany

[21] Appl. No.: 470,372

[22] Filed: Jun. 6, 1995

Related U.S. Application Data

[63] Continuation of Ser. No. 252,297, Jun. 1, 1994, abandoned.

[30] Foreign Application Priority Data

Jun. 8, 1993 [DE] Germany .................. 43 19 039.1

[51] Int. Cl.$^6$ .................................................. C07D 401/04
[52] U.S. Cl. ........................................ 546/199; 544/116
[58] Field of Search .............................. 546/199; 514/322

[56] References Cited

U.S. PATENT DOCUMENTS 4,031,226  6/1977  Soudijn .................................. 424/267

FOREIGN PATENT DOCUMENTS 0092391  10/1983  European Pat. Off. .
0173331  5/1986  European Pat. Off. .

OTHER PUBLICATIONS

Wlodawev, A & Erickson, J W 'Structure—based inhibitors of HIV–1 protease' Annv. Rev. Biochem, 1993 62 543–85.

Methods in Enzymology, vol. XXXIV, "Affinity Techniques, Enzyme Purification: Part B", Bovine Trypsin and Thrombin, Hixson, Jr. and A. H. Nishikawa, pp. 440–448, Academic Press, 1974.

Methods in Enzymology, vol. XXXIV, "Affinity Techniques, Enzyme Purification: Part B", Chymotrypsin(S), Tomlinson, et al., pp. 415–420, Academic Press 1974.

Affinity Chromatography, Biospecific Sorption; "Affinity Chromatography of Chymotrypsin on Soybean Trypsin Inhibitor Sepharose: Applications In Genetics And Nuclide Labelling", Gabel, Kasche, Amneus and Lundqvist, pp. 99–102, Pergamon Press, 1977.

Applied Microbiology and Biotechnology, Springer–Verlag 1979, Biotechnol. 6.; p. 195 (1979); "Recovery of Free Enzymes from Product Liquors by Bio–Affinity Adsorption: Trypsin Binding by Immobilised Soybean Inhibitor", Halling and Dunnill.

The Journal of Biological Chemistry, vol. 255, No. 15, Aug. 10, 1980, p. 7089, "Human Red Cell Purine Nucleoside Phosphorylase, Purification By Biospecific Affinity Chromatography and Physical Properties", Osborne, Mar. 17, 1980.

Hoppe–Seyler's Z. Physiol. Chem., vol. 361, p. 543, Apr. 1980, "Purification of Human and Bovine Alkaline Phosphatases by Affinity Chromatograph", Mossner, Bool and Pfleiderer.

Analytical Biochemistry, vol. 107, p. 341, (1980), "Affinity Chromatographic Sorting of Carboxypeptidase A and its Chemically Modified Derivatives", Cueni, Bazzone, Riordan & Vallee, Mar. 31, 1980.

Hoppe–Seyler's Z. Physiol. Chem., vol. 359, p. 1019, Aug 1978, "Affinity Chromatograph of Bovine Bran β–Hexosaminidases with Substrate As Affinity ligand"., Lisman and Overdijk, May 1978.

Biochem. J. (1978), vol. 175, p. 125, "Purification of the Hexokinases by Affinity Chromatography on Sepharose--N–Aminoacylglucosamine Derivatives", Wright, Warsy, Holroyde and Trayer, Feb. 1978.

Archives of Biochemistry and Biophysics, vol. 198, No. 2, Dec., 1979, p. 533, "Quantitative Affinity Chromatograph of α–Chymotrypsin", Dunn and Gilbert, Aug. 10, 1979.

Understanding Enzymes, Third Ed. (Horwood Press, 1991), pp. 309–310, Trevor Palmer.

Potent and Selective Inhibition of HIV–1 Replication Invitro By a Novel Series of Tibo Derivatives, vol. 343, Nature, Feb. 1, 1990, pp. 470–473, Rudi Pauwels, et al.

Journal of Virological Methods, vol. 22, 1988, pp. 309–317; "Antibodies to Human Cytomegalovirus Structural Polypeptides . . . ", M. P. Landini et al.

The EMBO Journal, vol. 7, No. 6, pp. 1785–1791, 1988; "Partial Purification and Substrate Analysis of Bacterially--Expressed HIV . . . ", J. Hansen et al.

Chemical Abstracts, 22–Physical Org. Chem., vol. 84, 1976, pp. 407 and 527; CA#59466u; "Aniline derivatives", I. Maruyama et al.

*Primary Examiner*—Jane Fan
*Assistant Examiner*—Evelyn Huang
*Attorney, Agent, or Firm*—Sprung Horn Kramer & Woods

[57] ABSTRACT

The present invention relates to substituted (2-oxo-1-benzimidazolinyl)-piperidines of the general formula (I)

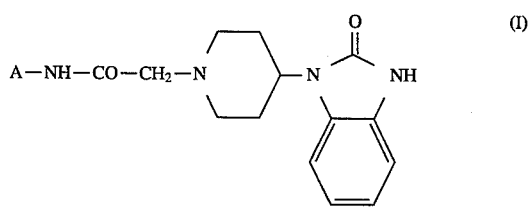

in which
the substituents have the meaning indicated in the description, to processes for their preparation and to their use as antiretroviral agents.

13 Claims, No Drawings

SUBSTITUTED (2-OXO-1-BENZIMIDAZOLINYL)-PEPERIDINES, PROCESS FOR THEIR PREPARATION, AND USE AS ANTI-RETROVIRAL AGENTS

This application is a continuation of application Ser. No. 08/252,297, filed on Jun. 1, 1994, abandoned.

The present invention relates to substituted (2-oxo-1-benimidazolinyl)-piperidines of the general formula (I)

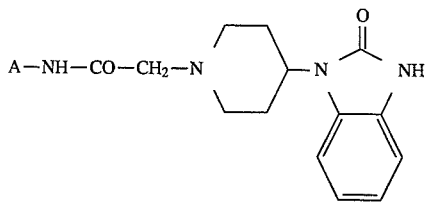

in which

A represents aryl having 6 to 10 carbon atoms, which is optionally substituted up to 4 times by identical or different substituents from the series consisting of halogen, carboxyl, nitro, hydroxyl, trifluoromethyl, cyano and straight-chain or branched alkyl, alkoxy, alkoxycarbonyl or alkylthio in each case having up to 8 carbon atoms, by cycloalkyl having 3 to 7 carbon atoms or by a group of the formula —P(O)—(OR$^1$)(OR$^2$), —CO—R$^3$, —CO—NR$^4$R$^5$, —SO$_2$R$^6$, —NR$^7$R$^8$, —SO$_2$NR$^9$R$^{10}$, —D—R$^{11}$ or —N=NR$^{12}$, in which R$^1$ and R$^2$ are identical or different and denote hydrogen or straight-chain or branched alkyl having up to 6 carbon atoms, R$^3$ denotes straight-chain or branched alkyl having up to 6 carbon atoms, morpholine or phenyl which is optionally substituted by halogen, R$^4$ and R$^5$ are identical or different and denote hydrogen, cycloalkyl having 3 to 7 carbon atoms, or straight-chain or branched alkyl having up to 6 carbon atoms, which is optionally substituted by phenyl, carboxyl or pyridyl, or by straight-chain or branched alkoxycarbonyl having up to 6 carbon atoms, or R$^4$ and R$^5$, together with the nitrogen atom, form a 5- to 7-membered, saturated heterocycle having up to 2 further hetero atoms from the series consisting of S, N and O, which in the case where a further nitrogen atom is present in the ring, is optionally also substituted via this, up to 3 times, by identical or different substituents from the series consisting of benzyl, formyl, carboxyl, straight-chain or branched alkoxycarbonyl having up to 5 carbon atoms and benzyloxycarbonyl or by a radical of the formula —CH$_2$—CO—NR$^{13}$R$^{14}$, in which R$^{13}$ and R$^{14}$ together with the nitrogen atom form a 5- to 7-membered heterocycle, R$^6$ denotes phenyl or straight-chain or branched alkyl having up to 6 carbon atoms, R$^7$ and R$^8$ are identical or different and denote hydrogen, phenyl, straight-chain or branched alkyl or acyl in each case having up to 6 carbon atoms, or a radical of the formula —C(S)—NR$^{15}$R$^{16}$, in which R$^{15}$ denotes hydrogen or methyl and R$^{16}$ denotes straight-chain or branched alkoxycarbonyl having up to 6 carbon atoms, R$^9$ and R$^{10}$ are identical or different and denote hydrogen, straight-chain or branched alkyl having up to 6 carbon atoms, phenyl or a 5- to 6-membered, saturated or unsaturated hetero-cycle having up to 3 further hetero atoms from the series consisting of S, N and O the cycles optionally being substituted by hydroxyl or carboxyl, or by straight-chain or branched alkyl, alkoxy or alkoxycarbonyl in each case having up to 6 carbon atoms, D denotes an oxygen or sulphur atom, R$^{11}$ and R$^{12}$ are identical or different and denote phenyl which is optionally substituted by halogen and their salts, a process for their preparation, and their use as antiretroviral agents.

Physiologically acceptable salts of the substituted (2-oxo-1-benzimidazolinyl)-piperidines can be salts of the substances according to the invention with mineral acids, carboxylic acids or sulphonic acids. Particularly preferred salts are e.g. those with hydrochloric acid, hyrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which can be mentioned are salts with customary bases, such as, for example, alkali metal salts (e.g. sodium or potassium salts), alkaline earth metal salts (e.g. calcium or magnesium salts) or ammonium salts, derived from ammonia or organic amines such as, for example, diethylamine, triethylamine, ethyldiisopropylamine, procaine, dibenzylamine, N-methylmorpholine, dihydroabietylamine, 1-ephenamine or methyl-piperidine.

The compounds according to the invention can exist in stereoisomeric forms, which either behave as image and mirror image (enantiomers), or which do not behave as image and mirror image (diastereomers). The invention relates both to the antipodes and to the racemic forms and the diastereomer mixtures. Like the diastereomers, the racemic forms can also be separated into the stereoisomerically homogeneous constituents in a known manner.

Heterocycle in general represents a 5- to 7-membered, preferably 5- to 6-membered, saturated or unsaturated ring which, as hetero atoms, can contain up to 3 oxygen, sulphur and/or nitrogen atoms. Preferred 5- and 6-membered rings are those containing an oxygen, sulphur and/or up to 2 nitrogen atoms. The following are preferably mentioned: thienyl, furyl, 1,2,4-thiadiazolyl, pyrrolyl, pyrazolyl, pyridyl, pyrimidyl, pyrazinyl, pyridazinyl, pyrrolidinyl, thiazolyl, oxazolyl, imidazolyl, pyrrolidinyl, piperidinyl, piperazinyl, tetrazolyl, morpholinyl or thiomorpholinyl.

Preferred compounds of the general formula (I) are those in which

A represents phenyl or naphthyl, each of which is optionally substituted up to 4 times by identical or different substituents from the series consisting of fluorine, chlorine, bromine, carboxyl, nitro, hydroxyl, trifluoromethyl, cyano and straight-chain or branched alkyl, alkoxy, alkoxycarbonyl or alkylthio in each case having up to 7 carbon atoms, by cyclopropyl, cyclopentyl or cyclohexyl, or by a group of the formula —P(O)—(OR$^1$)(OR$^2$), —CO—R$^3$, —CO—NR$^4$R$^5$, —SO$_2$R$^6$, —NR$^7$R$^8$, —SO$_2$NR$^9$R$^{10}$, —D—R$^{11}$ or —N=NR$^{12}$, in which R$^1$ and R$^2$ are identical or different and denote hydrogen or straight-chain or branched alkyl having up to 5 carbon atoms, R$^3$ denotes straight-chain or branched alkyl having up to 5 carbon atoms, morpholine or phenyl which is optionally substituted by fluorine, chlorine or bromine, R⁴ and R⁵ are identical or different and denote hydrogen, cyclopropyl, cyclopentyl, cyclohexyl or straight-chain or branched alkyl having up to 5 carbon atoms, which is optionally substituted by phenyl, carboxyl or pyridyl, or by straight-chain or branched alkoxycarbonyl having up to 5 carbon atoms, or R⁴ and R⁵, together with the nitrogen atom form a piperazine, morpholine or piperidine ring which, if appropriate in the case of the piperazine ring, is optionally also substituted via the nitrogen atom, up to 2 times, by identical or different substituents from the series consisting of benzyl, formyl, carboxyl, straight-chain or branched alkoxycarbonyl having up to 4 carbon atoms and benzyloxycarbonyl or by a radical of the formula —CH₂—CO—NR¹³R¹⁴, in which R¹³ and R¹⁴, together with the nitrogen atom, form a piperazine, piperidine or pyrrolidine ring, R⁶ denotes phenyl or straight-chain or branched alkyl having up to 5 carbon atoms, R⁷ and R⁸ are identical or different and denote hydrogen, phenyl, straight-chain or branched alkyl or acyl in each case having up to 5 carbon atoms, or a radical of the formula —C(S)—NR¹⁵R¹⁶, in which R¹⁵ denotes hydrogen or methyl and R¹⁶ denotes straight-chain or branched alkoxycarbonyl having up to 5 carbon atoms, R⁹ and R¹⁰ are identical or different and denote hydrogen, straight-chain or branched alkyl having up to 5 carbon atoms, phenyl or a pyrimidine, pyridyl, thiazolyl or 1,2,4-thiadiazolyl ring, the cycles optionally being substituted by hydroxyl or carboxyl, or by straight-chain or branched alkyl, alkoxy or alkoxycarbonyl in each case having up to 5 carbon atoms, D denotes an oxygen or sulphur atom, R¹¹ and R¹² are identical or different and denote phenyl which is optionally substituted by fluorine, chlorine or bromine and their salts.

Particularly preferred compounds of the general formula (I) are those in which

A represents phenyl or naphthyl, each of which is optionally substituted up to 4 times by identical or different substituents from the series consisting of fluorine, chlorine, bromine, iodine, carboxyl, nitro, hydroxyl, trifluoromethyl, cyano and straight-chain or branched alkyl, alkoxy, alkoxycarbonyl or alkylthio in each case having up to 6 carbon atoms, by cyclopropyl, cyclopentyl or cyclohexyl, or by a group of the formula —P(O)—(OR¹)(OR²), —CO—R³, —CO—NR⁴R⁵, —SO₂R⁶, —NR⁷R⁸, —SO₂NR⁹R¹⁰, —D—R¹¹ or —N=NR¹², in which R¹ and R² are identical or different and denote hydrogen or straight-chain or branched alkyl having up to 4 carbon atoms, R³ denotes straight-chain or branched alkyl having up to 4 carbon atoms, morpholine or phenyl which is optionally substituted by fluorine, chlorine or bromine, R⁴ and R⁵ are identical or different and denote hydrogen, phenyl, cyclopropyl, cyclopentyl, cyclohexyl or straight-chain or branched alkyl having up to 5 carbon atoms, which is optionally substituted by phenyl, carboxyl or pyridyl, or by straight-chain or branched alkoxycarbonyl having up to 4 carbon atoms, or R⁴ and R⁵, together with the nitrogen atom, form a piperazine, morpholine or piperidine ring which, if appropriate in the case of the piperazine ring, is optionally also substituted via the nitrogen atom, up to 2 times, by identical or different substituents from the group consisting of benzyl, formyl, carboxyl, straight-chain or branched alkoxycarbonyl having up to 3 carbon atoms and benzyloxycarbonyl, or by a radical of the formula —CH₂—CO—NR¹³R¹⁴, in which R¹³ and R¹⁴, together with the nitrogen atom, form a piperazine, piperidine or pyrrolidine ring, R⁶ denotes phenyl or straight-chain or branched alkyl having up to 4 carbon atoms, R⁷ and R⁸ are identical or different and denote hydrogen, phenyl, straight-chain or branched alkyl or acyl in each case having up to 4 carbon atoms, or a radical of the formula —C(S)—NR¹⁵R¹⁶, in which R¹⁵ denotes hydrogen or methyl and R¹⁶ denotes straight-chain or branched alkoxycarbonyl having up to 4 carbon atoms, R⁹ and R¹⁰ are identical or different and denote hydrogen, straight-chain or branched alkyl having up to 4 carbon atoms, phenyl or a pyrimidine, pyridyl, thiazolyl or 1,2,4-thiadiazolyl ring, the cycles optionally being substituted by hydroxyl or carboxyl, or by straight-chain or branched alkyl, alkoxy or alkoxycarbonyl in each case having up to 4 carbon atoms, D denotes n oxygen or sulphur atom, R¹¹ and R¹² are identical or different and denote phenyl which is optionally substituted by fluorine, chlorine or bromine and their salts.

A process for the preparation of the compounds of the general formula (I) according to the invention has additionally been found, characterized in that compounds of the general formula (II)

A—NH—CO—CH₂—L  (II)

in which

A has the abovementioned meaning and

L represents a typical leaving group, preferably chlorine or bromine, are reacted with 4-(2-oxo-1-benzimidazolinyl)-piperidine of the formula (III)

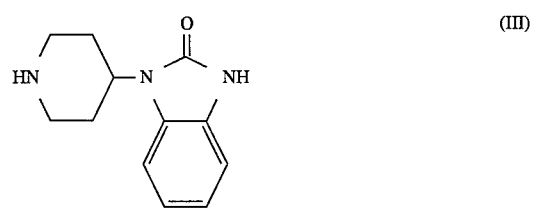

in inert solvents, if appropriate in the presence of a base and/or auxiliary, and the substituents mentioned under A are optionally derivatized by customary methods, such as, for example, alkylation, acylation, hydrolysis, hydrogenation, amidation or sulphonamidation.

The process according to the invention can be illustrated by way of example by the following reaction scheme:

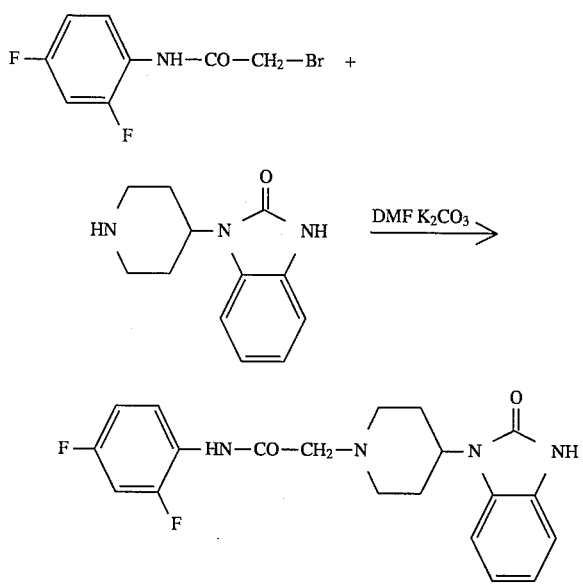

Suitable solvents are the customary inert solvents which do not change under the reaction conditions. These preferably include organic solvents such as ethers, e.g. diethyl ether, glycol monomethyl ether or glycol dimethyl ether, dioxane or tetrahydrofuran, or hydrocarbons such as benzene, toluene, xylene, cyclohexane or mineral oil fractions or halogenohydrocarbons such as dichloromethane, chloroform, carbon tetrachloride, or dimethyl sulphoxide, dimethylformamide, hexamethylphosphoramide, ethyl acetate, pyridine, triethylamine or picoline. It is also possible to use mixtures of the solvents mentioned. Dichloromethane, chloroform, dimethylformamide or tetrahydrofuran is particularly preferred.

Bases which can be employed for the process according to the invention are in general inorganic or organic bases. These preferably include alkali metal hydroxides such as, for example, lithium hydroxide, sodium hydroxide or potassium hydroxide, alkaline earth metal hydroxides such as, for example, barium hydroxide, alkali metal carbonates such as sodium carbonate or potassium carbonate, alkaline earth metal carbonates, such as calcium carbonate or caesium carbonate, or alkali metal or alkaline earth metal alkoxides or amides such as sodium methoxide or potassium methoxide, sodium ethoxide or potassium ethoxide or potassium tert-butoxide, or lithium diisopropylamide (LDA), or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, N-methylpiperidine or morpholine. It is also possible to employ as bases alkali metals, such as sodium, or their hydrides such as sodium hydride. Triethylamine or N-methylmorpholine are preferred.

In general, the base is employed in an amount from 0.05 mol to 10 mol, preferably from 1 mol to 2 mol, relative to 1 mol of the compounds of the formula (III).

The process according to the invention is in general carried out in a temperature range from −100° C. to +100° C., preferably from 0° C. to 80° C.

The process according to the invention is in general carried out at normal pressure. However, it is also possible to carry out the process at elevated pressure or at reduced pressure (e.g. in a range from 0.5 to 5 bar).

Auxiliaries employed are preferably condensing agents which can also be bases, in particular if the carboxyl group is present activated as the anhydride. Those preferred here are the customary condensing agents such as carbodiimides, e.g. N,N'-diethyl-, N,N'-diisopropyl or N,N'-dicyclohexylcarbodiimide, N-(3-dimethylaminoiso-propyl)-N'-ethyl-carbodiimide hydrochloride, N-cyclohexyl-N'-(2-morpholinoethyl)-carbodiimide metho-p-toluenesulphonate, or carbonyl compounds such as carbonyldiimidazole, or 1,2-oxazolium compounds such as 2-ethyl-5-phenyl-1,2-oxazolium-3-sulphate or 2-tertbutyl- 5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluorophosphate or 1-hydroxybenzotriazole.

Additionally, for example, alkali metal carbonates, e.g. sodium carbonate or potassium carbonate or sodium hydrogen carbonate or potassium hydrogen carbonate, or organic bases such as trialkylamines, e.g. triethylamine, ethyldiisopropylamine, N-ethylmorpholine, N-methylpiperidine or N-methylmorpholine can be employed. N-Methylmorpholine is preferred.

The auxiliaries are employed in an amount from 1.0 mol to 3.0 mol, preferably 1.0 to 1.2 mol, relative in each case to 1 mol of the compounds of the general formula (III).

The reactions are carried out in a temperature range from −30° C. to 100° C., preferably at 0° C. to 30° C. and at normal pressure.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from −20° C. to +100° C. preferably from 0° C., to +80° C.

In general, the hydrolysis is carried out at normal pressure. However, it is also possible to work at reduced pressure or at elevated pressure (e.g. from 0.5 to 5 bar ).

When carrying out the hydrolysis, the base is in general employed in an amount from 1 to 3 mol, preferably from 1 to 1.5 mol, relative to 1 mol of the ester. Molar amounts of the reactants are particularly preferably used.

The hydrolysis of tert-butyl esters is in general carried out using acids, such as, for example, hydrochloric acid or trifluoroacetic acid, in the presence of one of the abovementioned solvents and/or water or mixtures thereof, preferably using dioxane, tetrahydrofuran or dichloromethane.

The removal of the amino protective groups can likewise be carried out according to a customary method using acids, such as, for example, hydrochloric acid or trifluoroacetic acid.

The removal of the amino protective groups is carried out in a manner known per se under acidic or basic conditions, or reductively by catalytic hydrogenation, for example using Pd/C in organic solvents such as ethers, e.g. tetrahydrofuran or dioxane, or alcohols, e.g. methanol ethanol or isopropanol.

The hydrolysis is in general carried out in a temperature range from 0° C. to 80° C., preferably from 0° C. to 40° C.

The hydrogenation is in general carried out at an elevated pressure of from 2 bar to 8 bar, preferably from 3 bar to 5 bar.

It is also possible, in particular in the case of acylamino protective groups, to remove these at room temperature and normal pressure in one of the abovementioned ethers, using hydrides, such as, for example, lithium aluminium hydride or sodium borohydride.

The removal of the benzyl protective groups is preferably carried out using ammonium formate/palladium/C in ethanol/water in a temperature range from 50° C. to 100° C., preferably at 80° C. and normal pressure.

The alkylation of amino groups is carried out either using sulphonic acid esters or substituted or unsubstituted $(C_1-C_8)$-dialkyl or $(C_1-C_8)$-diaryl sulphonates, preferably methyl iodide or dimethyl sulphate, or using formaldehyde/sodium borohydride in one of the abovementioned ethers, preferably tetrahydrofuran, in the presence of acids.

The alkylation is in general carried out in one of the abovementioned solvents, preferably in dimethylformamide in temperature range from 0° C. to +70° C., preferably from 0° C. to +30° C. and normal pressure.

The reductions of the carbonyl functions of the compounds of the general formulae (IV) and (VII) and partially occurring intermediates containing this group are in general carried out using reducing agents, such as, for example, lithium aluminiumhydride, using borane solution in tetrahydrofuran or using borane-dimethyl sulphide (complex in tetrahydrofuran) in a temperature range from 0° C. to +70° C., preferably from +20° C. to +65° C. and normal pressure, and subsequently taking up in acids. Borane solution in tetrahydrofuran is preferred.

Suitable acids for individual process steps are in general protic acids such as, for example, hydrochloric acid or sulphuric acid. Sulphuric acid is preferably employed.

The acid is in general employed in an amount from 1 mol to 20 mol, preferably from 1 mol to 5 mol, in each case relative to 1 mol of the reactant.

The reactions are in general carried out in a temperature range from −20° C. to +80° C., preferably from 0° C. to +60° C.

In general, the reaction is carried out at normal pressure. However, it is also possible to work at reduced pressure or at elevated pressure (e.g. from 0.5 to 5 bar).

The compounds of the general formula (II) are known in some cases or are new and can then be prepared, for example, by reacting compounds of the general formula (IV)

  (IV)

in which

A has the abovementioned meaning, with compounds of the general formula (V)

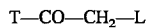  (V)

in which

L has the abovementioned meaning and

T represents halogen, preferably chlorine, in one of the abovementioned solvents and bases, preferably acetonitrile and potassium carbonate, in a temperature range from 0° C. to +80° C., preferably from +15° C. to +30° C., and normal pressure.

The compounds of the general formulae (IV) and (V) are known.

The inhibitors described here are inhibitors of HIV protease and can be employed as such for all purposes for which enzyme inhibitors are suitable. This is, for example, use in diagnostics to improve the precision and selectivity of enzyme activity measurements. In affinity chromatography, they can be used as affinity labels and in research can be used for elucidating reaction mechanisms and the specificity of enzymatic reactions.

Moreover, it has surprisingly been found that the compounds of the general formula (I) have an extremely potent action against retroviruses. This is confirmed by an HIV-specific protease enzyme test.

The results of the examples shown below were determined by the HIV test system described in the following literature references [cf. Hansen, J., Billich, S., Schulze, T., Sukrow, S. and Mölling, K. (1988), EMBO Journal, Vol. 7, No. 6, pp. 1785–1791]: purified HIV protease was incubated with synthetic peptide which imitates a cleavage site in the Gag precursor protein and represents an in vivo cleavage site of the HIV protease. The resultant cleavage products of the synthetic peptide were analysed by means of reverse phase high performance liquid chromatography (RP-HPLC). The $IC_{50}$ values indicated relate to the substance concentration which, under the abovementioned test conditions, causes a 50% inhibition of the protease activity.

HIV infection in cell culture

The HIV test was carried out with slight modifications according to the method of Pauwels et al. [cf. Journal of Virological Methods 20, (1988), 309–321].

Normal human blood lymphocytes (PBLs) were concentrated by means of Ficoll Hypaque and stimulated with phytohaemagglutinin (90 μ/ml) and interleukin-2 (40 U/ml) in RPMI 1640 and 20% foetal calf serum. For infection with the infectious HIV, PBLs were pelleted and the cell pellet was then suspended in 1 ml of HIV virus adsorption solution and incubated for 1 hour at 37° C.

Alternatively, HIV-susceptible H9 cells were employed instead of normal human blood lymphocytes for testing the antiviral effects of the compounds according to the invention.

The virus adsorption solution was centrifuged and the infected cell pellet was taken up in growth medium such that the concentration was $1\times10^5$ cells per ml. The cells infected in this way were pipetted at $15 \times 10^4$ cells/well into the wells of 96-well microtitre plates.

The first vertical row of the microtitre plate contained only growth medium and cells which had not been infected, but otherwise treated just as described above (cell control). The second vertical row of the microtitre plate contained only HIV-infected cells (virus control) in growth medium. The other wells contained the compounds according to the invention at different concentrations, starting from the wells of the 3rd vertical row of the microtitre plates, from which the test substances were diluted $2^{10}$ times in 2 steps.

The test batches were incubated at 37° C. until the syncytia formation typical of HIV occurred in the untreated virus control (between days 3 and 6 after infection), which was then assessed by microscopy. Under these test conditions, about 20–50 syncytia result in the untreated virus control, while the untreated cell control contained no syncytia.

The $IC_{50}$ values were determined as the concentration of the treated and infected cells at which 50% (about 10–20 syncytia) of the virus-induced syncytia were suppressed by the treatment with the compound according to the invention.

It has now been found that the compounds according to the invention protect HIV-infected cells from virus-induced cell destruction.

The compounds according to the invention are useful active compounds in human and veterinary medicine for the treatment and prophylaxis of disorders caused by retroviruses.

Examples of indication areas in human medicine which may be mentioned are:

1) The treatment and prophylaxis of human retrovirus infections.

2) For the treatment or prophylaxis of disorders (AIDS) caused by HIV I (human immunodeficiency virus; formerly called HTLV III/LAV) and HIV II and the stages associated therewith such as ARC (AIDS-related complex) and LAS (lymphadenopathy syndrome) as well as the immunodeficiency and encephalopathy caused by this virus. 3) For the treatment or the prophylaxis of an HTLV-I or HTLV-II infection. 4) For the treatment or the prophylaxis of the AIDS-carrier state (AIDS-transmitter state).

Examples of indications in veterinary medicine which may be mentioned are:

Infections with
- a) maedi-visna (in sheep and goats)
- b) progressive pneumonia virus (PPV) (in sheep and goats)
- c) caprine arthritis encephalitis virus (in sheep and goats)
- d) zwoegersiekte virus (in sheep)
- e) infectious anaemia virus (of the horse)
- f) infections caused by feline leukaemia virus
- g) infections caused by feline immunodeficiency virus (FIV)
- h) infections caused by simian immunodeficiency virus (SIV)

From the indication area in human medicine, the above-mentioned items 2, 3 and 4 are preferred.

The present invention includes pharmaceutical preparations which, in addition to non-toxic, inert pharmaceutically suitable excipients, contain one or more compounds of the formula (I) or which consist of one or more active compounds of the formula (I), and processes for the production of these preparations.

The active compounds of the formula (I) should be present in the abovementioned pharmaceutical preparations in a concentration of about 0.1 to 99.5% by weight, preferably of about 0.5 to 95% by weight, of the total mixture.

The abovementioned pharmaceutical preparations can also contain other pharmaceutical active substances apart from the compounds of the formula (I).

The abovementioned pharmaceutical preparations are produced in a customary manner according to known methods, e.g. by mixing the active compound or compounds with the excipient or excipients.

In general, it has proven advantageous both in human and in veterinary medicine to employ the active compound or compounds in total amounts of about 0.5 to about 500 mg/kg, preferably 1 to 100 mg/kg, of body weight every 24 hours, if appropriate in the form of several individual doses, to achieve the desired results. An individual dose contains the active compound or compounds preferably in amounts of about 1 to about 80 mg/kg, in particular 1 to 30 mg/kg, of body weight. However, it may be necessary to depart from the doses mentioned, mainly depending on the type and the body weight of the subject to be treated, the nature and severity of the disorder, the type of preparation and the administration of the medicament and the period or interval within which administration takes place.

Explanations for the experimental section:
TLC systems:
Stationary phase:
Merck TLC ready-to-use silica gel 60 F-254 plates, 5×10 cm, layer thickness 0.25 mm, item No. 5719
Mobile phases (in the test as "TLC system")
I: toluene/ethyl acetate 1:1
II: ethyl acetate/acetone 3:1
III: $CH_2Cl_2$/methanol 9:1
IV: $NH_3$/$CH_2Cl_2$/methanol 0.2:9:1
V: HOAc/$CH_2Cl_2$/methanol 0.2:9:1
VI: glacial acetic acid/n-butanol/$H_2O$ 1:3:1

HPLC systems:
HPLC system I:
Merck Lichrosorb$^R$ RP-18 column, 250-4, 10 μM, Cat. No. 50334
Eluent in system I
A: pH 7.00 phosphate buffer, Merck item No. 9439/$H_2O$ 1:50
B: acetonitrile A/B w/w 1:1, flow rate: 2 ml/min, isocratic,
Detection: 214 nm HPLC system II:
Column: Nucleosil 120-5 C18, 5 μM, 125×4 mm
Eluent: A=0.01M $H_3PO_4$, B=acetonitrile
Eluent programme: 0-1 min: 10% B 1-9 min: gradient with 10% B/min 9-13 min: 90% B
Flow rate: 2 ml/min
Temperature: room temperature
Injection volume: 5 μl
Sample: about 1 mg/ml
Detection: UV diode array at 210 nm Index of the abbreviations used
General analytical methods

| | |
|---|---|
| TLC | thin-layer chromatography |
| GC | gas chromatography |
| HPLC | high-pressure liquid chromatography |
| CC | column chromatography |
| LC | liquid chromatography |
| NMR | nuclear spin resonance spectroscopy (protons) |
| MS | mass spectrometry (electron impact ionization) |
| (+) FAB-MS | fast atomic bombardment mass spectrometry, positive ions, matrix substance: m-nitrobenzyl alcohol |
| MS-DCI | mass spectrometry, chemical ionization |

| Reagents | |
|---|---|
| NEM | N-ethylmorpholine |
| NMM | N-methylmorpholine |
| TEA | triethylamine |
| TFA | trifluroracetic acid |

| Solvents | |
|---|---|
| HOAc | acetic acid |
| DMF | dimethylformamide |
| EtOAc | ethyl acetate |
| MeOH | methanol |
| EtOH | ethanol |
| THF | tetrahydrofuran |
| DMSO | dimethyl sulphoxide |
| HMPT | hexamethylphosphoramide |
| $CH_2Cl_2$ | dichloromethane |
| $NH_3$ | ammonia solution (25% aqueous) |

| Protective groups | |
|---|---|
| Boc | tert-butoxycarbonyl |
| Z | benzyloxycarbonyl |
| DNP | dinitrophenyl |
| Fmoc | 9-fluoromethoxycarbonyl |
| OEt | ethyl ester |
| OMe | methyl ester |

Starting Compounds

EXAMPLE I

1-Bromo-2-(2,4-difluorophenyl)amino-2-oxoethane

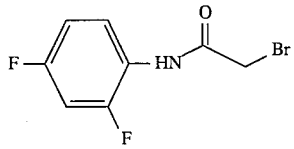

5.16 g (40 mmol) of 2,4-difluoroaniline and 6.3 g (40 mmol) of bromoacetyl chloride are treated in 200 ml of dichloromethane with 5.17 g (40 mmol) of Hünig base. After 4 h, the mixture is washed twice with 1N hydrochloric acid and once with water, dried (MgSO$_4$) and concentrated.

Yield: 7.6 g (70%)

$^1$H-NMR (CDCl$_3$): δ=4.22 (s, 2H); 6.92 (m, 2H); 8.20 (m, 1H); 8.40 (br, NH).

EXAMPLE II

1-Chloro-2-(2-carboxy-4-chlorophenyl)amino-2-oxoethane

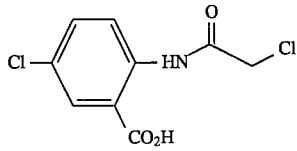

12.5 g (73 mmol) of 2-amino-5-chlorobenzoic acid are initially introduced into 500 ml of acetonitrile and treated with 9.0 g (80 mmol) of chloroacetyl chloride with stirring, the temperature being kept at 20°–25° C. (ice-bath). 22 g (0.16 mol) of finely pulverized potassium carbonate are then introduced and the mixture is stirred overnight at room temperature. The batch is adjusted to pH 2 with dilute hydrochloric acid and the acetonitrile is stripped off on a rotary evaporator. The precipitate is filtered off with suction and washed well with water. The crude product is treated with sodium bicarbonate solution and stirred. Insoluble matter is filtered off with suction and the filtrate acidified with dilute hydrochloric acid to pH 2. The precipitated product is filtered off with suction and dried. Yield: 7 g (77.3% of theory) M.p.: 188° C.

Preparation Examples

Example 1

1-[2-(2,4-Difluorophenyl)amino-2-oxo-ethyl]-4-(2-oxo-1-benzimidazolinyl)piperidine

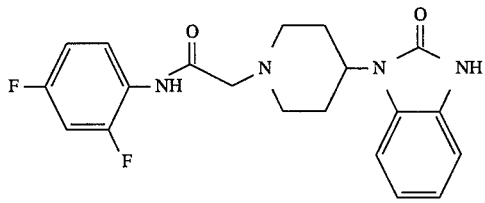

4 g (16 mmol) of the bromoacetanilide from Example I and 4.2 g (19 mmol) of 4-(2-oxo-1-benzimidazolinyl)piperidine in 50 ml of dimethylformamide are stirred at RT for 18 h with 2.6 g (19 mmol) of potassium carbonate. The solid is then filtered off with suction, the filtrate is partitioned between ethyl acetate and water, and the aqueous phase is extracted 3 times with ethyl acetate. The organic phases are combined, washed with saturated sodium chloride solution, dried (MgSO$_4$) and concentrated. The residue obtained is triturated with ether, and the solid is filtered off and then recrystallized from methanol.

Yield: 4.8 g (77.6% of theory) TLC system I: R$_f$=0.16 HPLC system I: R$_t$=4.07 min (+) FAB-MS: m/e=387 M+H

Example 2

1-[2-(2-Carboxy-4-chlorophenyl)amino-2-oxoethyl]-4-(2-oxo-1-benzimidazolinyl)piperidine

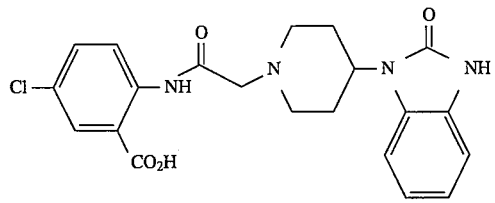

7.94 g (32 mmol) of the compound from Example II and 8.26 g (40 mmol) of 4-(2-oxo-1-benzimidazolinyl)piperidine (Aldrich) are initially introduced in 120 ml of DMF. The mixture is treated with 5.52 g (40 mmol) of potassium carbonate and 0.45 g (3 mmol) of sodium iodide and stirred overnight at room temperature. The batch is diluted with 600 ml of H$_2$O and the product is precipitated at pH 5 by dropwise addition of 33 ml of 1N hydrochloric acid. The precipitate is filtered off with suction, stirred with 300 ml of diethyl ether and dried in a high vacuum.

Yield: 12.3 g (89.4% of theory) TLC system I: R$_f$=0.36 TLC system III: R$_f$=0.25 TLC system V: R$_f$=0.39 HPLC system I: R$_t$=0.93 min HPLC system II: R$_t$=46.565 min (+) FAB-MS: m/e=429/431 (M+H)

Example 3

1-[2-(2-Aminophenyl)amino-2-oxoethyl]-4-(2-oxo-1-benzimidazolinyl)piperidine

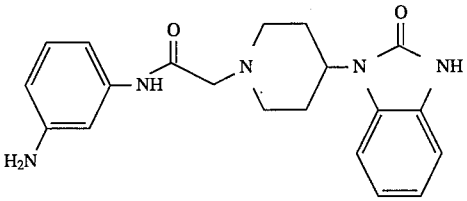

4 g (10.12 mmol) of 1-[2-(2-nitrophenyl)amino-2-oxoethyl]-4-(2-oxo-1-benzimidazolinyl)piperidine are dissolved in 40 ml of DMF. After addition of 400 mg of 10% Pd/C (Aldrich), the mixture is hydrogenated at 3 bar until reaction is complete (TLC). The catalyst is filtered off and all solvent is stripped off in a high vacuum. The crude product is coevaporated several times with methanol. The crystals obtained are stirred in methanol, filtered off with suction and dried at 30° C. in a high vacuum.

Yield: 3.1 g (83.8% of theory) TLC system II: $R_f$=0.47 TLC system IV: $R_f$=0.51 HPLC system I: $R_t$=1.77 min (+) FAB-MS: m/e 366 (M+H)

Example 4

1-[2-(4-Amino-2-chlorophenyl)amino-2-oxoethyl]-4-(2-oxo-1-benzimidazolinyl)piperidine

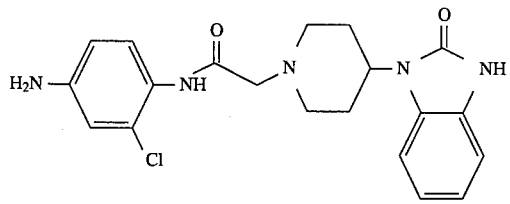

4.29 g (10mmol) of 1-[2-(2-chloro-5-nitrophenyl)amino-2-oxoethyl]- 4-(2-oxo-1-benzimidazolinyl)piperidine, 3.21 g (60 mmol) of ammonium chloride, 10 ml of water and 60 ml of methyl glycol are mixed together and the suspension is heated to 110° C. with stirring. After addition of 20 ml of DMF and 3.35 g (60 mmol) of iron filings, the mixture is boiled under reflux for 1 h. The solvent is completely stripped off in a high vacuum. The residue is stirred with 150 ml of dichloromethane and 100 ml of water and filtered off. The filtrate is separated in a separating funnel, and the aqueous phase is extracted two more times with dichloromethane. The combined organic phases are washed with saturated sodium bicarbonate solution, dried over sodium sulphate and the solvent is evaporated in a rotary evaporator. The solid obtained is stirred with diethyl ether, filtered off with suction and dried.

Yield: 480 mg (12% of theory)

The dichloromethane/water-insoluble solid is stirred hot with 150 ml of methanol, filtered off and washed with 50 ml of hot methanol. The filtrates are concentrated to dryness and the residue is filtered off with suction after triturating with diethyl ether and dried.

Yield: 2.48 g (62% of theory) Total yield: 2.96 g (74% of theory) TLC (9/1): $R_f$=0.43 HPLC: 2.11 min (+) FAB-MS: m/e 400/402 M+H The compounds shown in Table 1 are prepared analogously to the procedures of Examples 1–4 and starting from the corresponding hemiacetamide derivatives and 4-(2-oxo-1-benzimidazolinyl)piperidine (Aldrich, Jansen).

The haloacetamide derivatives used are synthesized from the appropriate arylamines and bromo- or chloroacetyl chloride analogously to Examples I and II. Some of the haloacetamide derivatives were bought in (Bader). The arylamines employed are either commercially available or are prepared by known methods (Houben-Weyl)—optionally via the nitro compound as a precursor. The nitro group is reduced to the amino group, for example, by catalytic hydrogenation or by reaction with base metals such as iron or zinc.

TABLE 1

| Ex. No. | V | W | X | Y | Z | TLC system/ $R_f$ value | HPLC system/ $R_t$ value (min.) | (+) FAB-MS m/e |
|---|---|---|---|---|---|---|---|---|
| 5 | H | H | H | Cl | Cl | I/0.27 | I/12.58 | 419/421 (M + H) |
| 6 | CH₃ | NO₂ | H | OH | H | I/0.60 | I/1.76 | 412 (M + H) |
| 7 | –CO–C₆H₄-o-Cl | H | H | CH₃ | H | I/0.68 | I/2.78 | 379 (M + H) |
| 8 | CH₃ | CH₃ | H | H | Cl | I/0.83 | I/19.16 | 523/525 (M + H) |
| 9 | CH₃ | H | H | H | H | I/0.26 | I/3.76 | 379 (M + H) |
| 10 | CH₃ | CH₃ | H | H | H | I/0.31 | I/3.21 | 365 (M + H) |
| 11 | H | Cl | H | H | H | I/0.50 | I/4.94 | 399/401 (M + H) |
| 12 | H | H | Cl | H | H | I/0.45 | I/2.61 | 399/401 (M + H) |
| 13 | CH₃ | H | H | H | CH₃O | I/0.50 | I/2.32 | 351 (M + H) |
| 14 | H | H | H | H | H | I/0.56 | I/4.89 | 381 (M + H) |
| 15 | NO₂ | H | H | H | H | I/0.43 | I/5.17 | 399/401 (M + H) |
| 16 | H | NO₂ | H | H | H | I/0.67 | I/3.21 | 396 (M + H) |
| 17 | H | CF₃ | H | H | H | I/0.65 | I/4.80 | 396 (M + H) |
| 18 | OH | H | H | H | H | I/0.47 | I/2.04 | 419 (M + H) |
| 19 | H₃C–CH₂–CH–CH–CH₃ | H | H | H | H | I/0.43 | I/6.30 | 367 (M + H) |
| 20 | –CH(CH₃)₂ | H | H | H | H | I/0.52 | I/4.93 | 407 (M + H) |
| 21 | –O–C₆H₅ | H | H | H | H | I/0.53 | I/8.22 | 393 (M + H) |
| 22 | ![structure] | H | H | H | –S–C₆H₅ | II/0.62 | I/8.31 | 443 (M + H) |
| 23 | NO₂ | H | H | H | –SO₂–C₆H₅ | II/0.41 | I/6.77 | 591 (M + H) |
| 24 | H | Cl | H | H | H | II/0.64 | I/4.26 | 536 (M + H) |
| 25 | H | Cl | H | H | Cl | II/0.45 | I/6.46 | 385/387 (M + H) |
| 26 | H | NC– | H | H | NC– | II/0.37 | I/2.77 | 419/421 (M + H) |
| 27 | H | H | H | H | –CO₂–CH₃ | II/0.58 | I/2.84 | 401 (M + H) |
| 28 | H | H | H | H | –CH₃ | II/0.42 | I/3.56 | 409 (M + H) |
| 29 | H | H | H | H | Cl | II/0.66 | I/2.31 | 365 (M + H) |
| 30 | H | Cl | H | H | NO₂ | II/0.66 | I/4.34 | 385/387 (M + H) |
| 31 | H | H | H | H | CF₃ | II/0.67 | I/5.22 | 430/432 (M + H) |
| 32 | H | H | H | H | –C(CH₃)₃ | II/0.64 | I/8.49 | 419 (M + H) |
| 33 | H | H | H | H | NC– | II/0.65 | I/2.57 | 407 (M + H) |
| 34 | H | H | H | H | –NO₂ | II/0.33 | I/3.33 | 376 (M + H) |
| 35 | H | H | H | H | –CO–CH₃ | II/0.61 | I/2.22 | 396 (M + H) |
|   |   |   |   |   |   |   |   | 393 (M + H) |

TABLE 1-continued

[Structure: phenyl ring with substituents W, V, Z, X, Y and NH—CO—CH2—N-piperidine-N-C(=O)—NH-phenyl]

| Ex. No. | V | W | X | Y | Z | TLC system/ $R_f$ value | HPLC system/ $R_t$ value (min.) | (+) FAB-MS m/e |
|---|---|---|---|---|---|---|---|---|
| 36 | H | H | H | H | —N—(CH$_3$)$_2$ | II/0.39 | I/2.96 | 394 (M + H) |
| 37 | H | H | H | H | —O—C$_6$H$_5$ | II/0.44 | I/6.91 | 443 (M + H) |
| 38 | H | H | H | H | —C$_6$H$_{11}$ | II/0.54 | I/17.83 | 433 (M + H) |
| 39 | H | H | H | H | —NH—CO—CH$_3$ | II/0.14 | I/1.57 | 408 (M + H) |
| 40 | H | H | H | H | —CO—NH$_2$ | II/0.10 | I/1.43 | 394 (M + H) |
| 41 | H | H | H | H | —SO$_2$—NH$_2$ | II/0.31 | I/1.59 | 430 (M + H) |
| 42 | H | H | H | H | [pyrimidine with CH$_3$O and NH—SO$_2$—] | II/0.30 | I/1.11 | 538 (M + H) |
| 43 | H | H | H | H | —N═N—C$_6$H$_5$ | II/0.69 | I/12.62 | 455 (M + H) |
| 44 | H | H | H | H | —CO—C$_6$H$_5$ | II/0.58 | I/4.66 | 455 (M + H) |
| 45 | Cl | H | H | H | H | II/0.69 | I/6.09 | 385/387 (M + H) |
| 46 | —CH$_3$ | —NO$_2$ | H | H | —OC$_2$H$_5$ | II/0.62 | I/3.16 | 410 (M + H) |
| 47 | H | H | H | H | H | II/0.54 | I/3.35 | 395 (M + H) |
| 48 | H | H | H | H | [thiazole with H$_5$C$_2$ and NH—SO$_2$—] | II/0.13 III/0.25 | I/0.93 | 542 (M + H) |
| 49 | NO$_2$ | H | H | H | —SC$_3$H$_7$ | II/0.63 | I/22.45 | 470 (M + H) |
| 50 | NO$_2$ | H | H | H | Cl | II/0.66 | I/9.70 | 430/432 (M + H) |
| 51 | —C$_2$H$_5$ | H | H | H | H | II/0.63 | I/4.21 | 379 (M + H) |
| 52 | CH$_3$ | H | H | H | Cl | II/0.66 | I/5.36 | 399/401 (M + H) |
| 53 | —CO—NH$_2$ | H | H | H | NO$_2$ | II/0.58 | I/2.65 | 439 (M + H) |
| 54 | —O—C$_4$H$_9$ | H | H | H | H | II/0.58 | I/9.19 | 423 (M + H) |
| 55 | —C(CH$_3$)$_3$ | H | H | H | H | II/0.43 | I/5.94 | 407 (M + H) |
| 56 | CF$_3$ | H | H | H | Cl | II/0.67 | I/10.97 | 453/455 (M + H) |
| 57 | —CO$_2$H | H | H | H | H | II/0.30 | I/0.96 | 395 (M + H) |
| 58 | —OCH$_3$ | H | H | H | Cl | II/0.73 | I/6.86 | 415/417 (M + H) |
| 59 | —CO$_2$C$_2$H$_5$ | H | H | H | H | II/0.55 | I/10.51 | 423 (M + H) |
| 60 | —CO—NH—CH$_3$ | H | H | H | H | II/0.62 | I/2.43 | 408 (M + H) |
| 61 | CH$_3$ | H | H | H | —NO$_2$ | II/0.60 | I/4.44 | 410 (M + H) |

TABLE 1-continued

| Ex. No. | V | W | X | Y | Z | TLC system/ $R_f$ value | HPLC system/ $R_t$ value (min.) | (+) FAB-MS m/e |
|---|---|---|---|---|---|---|---|---|
| 62 | —CO—NH—CH$_2$—COOC$_2$H$_5$ | H | H | H | H | II/0.47 | I/2.65 | 480 (M + H) |
| 63 | —CO—NH$_2$ | H | H | H | H | II/0.51 | I/1.96 | 394 (M + H) |
| 64 | —CO$_2$H | H | Cl | H | H | III/0.14 | II/4.585 | 429/431 (M + H) |
| 65 | —SO$_2$—NH—C$_6$H$_4$-o-COOCH$_3$ | H | H | H | H | II/0.47 | I/11.48 | 564 (M + H) |
| 66 | Cl | H | H | H | CF$_3$ | II/0.61 | I/11.87 | 453/455 (M + H) |
| 67 | H | H | H | H | HO— | III/0.66 | I/2.14 | 367 (M + H) |
| 68 | Cl | H | H | H | NO$_2$ | II/0.20 | I/8.40 | 430/432 (M + H) |
| 69 | Cl | H | H | H | Br | II/0.47 | I/4.90 | 429/431 (M + H) |
| 70 | —CO—C$_6$H$_5$ | H | H | H | Cl | II/0.59 | I/19.50 | 489/391 (M + H) |
| 71 | H | H | H | H | pyrazole-NH—SO$_2$— | II/0.28 | I/1.05 | 513 (M + H) |
| 72 | H | H | H | H | pyrimidine-NH—SO$_2$— | II/0.32 | I/0.87 | 508 (M + H) |
| 73 | H | H | H | H | —NH$_2$ | II/0.36 | I/1.74 | 366 (M + H) |
| 74 | H | Cl | H | H | Br | II/0.57 | I/7.57 | 463/465 (M + H) |
| 75 | H | NO$_2$ | H | H | Cl | II/0.64 | I/4.66 | 430/432 (M + H) |
| 76 | CH$_3$ | NH$_2$ | H | H | H | II/0.59 | I/1.96 | 380 (M + H) |
| 77 | NH$_3$ | H | H | H | —S—C$_3$H$_7$ | II/0.27 | I/5.08 | 440 (M + H) |
| 78 | H | —N(CH$_3$)$_2$ | H | H | H | II/0.43 | I/3.46 | 394 (M + H) |
| 79 | H | H | H | H | —NH—C$_6$H$_5$ | II/0.57 | I/5.11 | 442 (M + H) |
| 80 | H | —N(C$_2$H$_5$)$_2$ | H | H | H | II/0.62 | I/6.87 | 506 (M + H) |
| 81 | —NH$_2$ | H | H | H | —SO$_2$C$_6$H$_5$ | II/0.47 | I/2.82 | 400/402 (M + H) |
| 82 | —NH$_2$ | H | H | H | Cl | III/0.33 | I/3.49 | 409 (M + H) |
| 83 | —CONH$_2$ | H | H | H | —NH$_2$ | II/0.29 | I/1.20 | 380 (M + H) |
| 84 | CH$_3$ | H | H | H | —NH$_2$ | III/0.56 | I/1.64 | 366 (M + H) |
| 85 | —NH$_2$ | H | H | H | H | II/0.19 | I/2.06 | 382 (M + H) |
| 86 | —OH | H | —NH$_2$ | H | —C$_2$H$_5$ | III/0.28 | I/1.09 | — |
| 87 | Br | H | H | Br | Br | II/0.59 | I/7.78 | 535/537/539 (M + H) |
| 88 | Cl | H | H | Br | Br | II/0.50 | I/5.74 | 541/543/545 (M + H) |
| 89 | Br | H | Br | Br | Cl | I/0.31 | I/6.05 | 541/543/545 (M + H) |

TABLE 1-continued

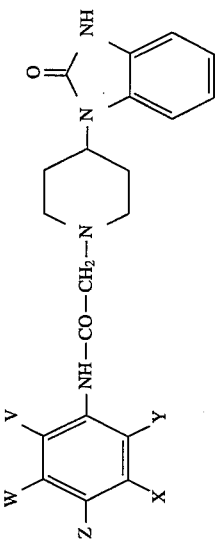

| Ex. No. | V | W | X | Y | Z | TLC system/ $R_f$ value | HPLC system/ $R_t$ value (min.) | (+) FAB-MS m/e |
|---|---|---|---|---|---|---|---|---|
| 90 | $NO_2$ | H | H | H | $-OCH_3$ | I/0.33<br>II/0.60 | I/5.78 | 426 (M + H) |
| 91 | Cl | H | H | Cl | Cl | I/0.37<br>II/0.69 | I/21.63 | 453/455/457 (M + H) |
| 92 | Cl | H | Cl | H | Cl | I/0.13<br>II/0.55 | I/5.52 | <u>453</u>/455/457 (M + H) |
| 93 | $CH_3$ | H | H | $CH_3$ | Br | I/0.25<br>II/0.54 | I/5.48 | 457/459 (M + H) |
| 94 | $-O-C_6H_5$ | H | H | H | Cl | I/0.15<br>II/0.51 | I/16.28 | 477/479 (M + H) |
| 95 | $-CO_2H$ | H | H | H | J | III/0.29 | | 521 (M + H) |
| 96 | $-CO-C_6H_5$ | H | Cl | H | H | I/0.10 | I/19.10 | 489/491 (M + H) |
| 97 | $-OCH_3$ | H | H | H | $NO_2$ | I/0.38<br>II/0.62 | I/5.50 | 426 (M + H) |
| 98 | $CH_3$ | H | $CH_3$ | H | H | II/0.07 | I/4.63 | 379 (M + H) |
| 99 | $-COOCH_3$ | H | H | H | Cl | I/0.39<br>II/0.61 | I/15.40<br>II/5.398 | 443/445 (M + H) |
| 100 | Br | H | H | H | $NO_2$ | II/0.54 | I/8.20 | 474/476 (M + H) |
| 101 | H | Cl | H | H | $-O-C_6H_4$-p-Cl | II/0.22<br>II/0.71 | I/17.47 | 511/513 (M + H) |
| 102 | $-CO_2H$ | H | $-NO_2$ | H | H | III/0.09 | I/3.42 | 440 (M + H) |
| 103 | H | F | H | H | H | I/0.06<br>II/0.61 | I/3.96 | 369 (M + H) |
| 104 | F | H | H | H | H | I/0.09<br>II/0.54 | I/15.40<br>II/5.498 | 443/445 (M + H) |
| 105 | $-COOCH_3$ | H | Cl | H | H | I/0.53 | I/6.50 | 414 (M + H) |
| 106 | $NO_2$ | H | H | H | F | I/0.66<br>II/0.89 | I/24.16 | 457/459 (M + H) |
| 107 | $-COOC_2H_5$ | H | Cl | H | H | I/0.26<br>II/0.71 | I/2.30 | 411 (M + H) |
| 108 | $-CONH_2$ | F | H | H | H | I/0.07<br>II/0.57 | I/4.86 | |
| 109 | F | H | F | H | H | I/0.14<br>II/0.60 | I/3.98 | 387 (M + H) |
| 110 | F | F | H | H | H | I/0.07<br>II/0.60 | | |

TABLE 1-continued

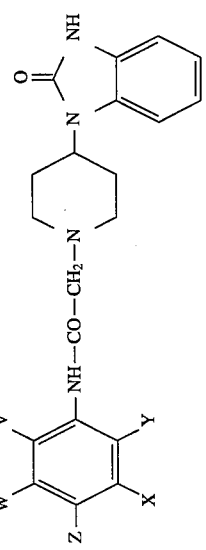

| Ex. No. | V | W | X | Y | Z | TLC system/ $R_f$ value | HPLC system/ $R_t$ value (min.) | (+) FAB-MS m/e |
|---|---|---|---|---|---|---|---|---|
| 111 | H | F | H | H | F | I/0.06<br>II/0.65 | I/3.63 | 387 (M + H) |
| 112 | F | H | F | F | H | II/0.14<br>II/0.64 | I/2.35 | 387 (M + H) |
| 113 | H | H | H | H | F | I/0.14<br>II/0.57 | I/2.98 | 369 (M + H) |
| 114 | —CONH$_2$ | H | H | H | Br | II/0.58 | I/3.29 | 472/474 (M + H) |
| 115 | —CONH$_2$ | H | H | H | Cl | I/0.12<br>II/0.50 | I/2.99 | 428/430 (M + H) |
| 116 | —CO—NH—(CH$_2$)$_2$—C$_6$H$_5$ | H | H | H | Cl | II/0.59 | I/13.86 | 532/534 (M + H) |
| 117 | H | CO$_2$H | H | H | Cl | V/0.08 | II/3.971 | 429/431 (M + H) |
| 118 | —CO—NH—CH$_2$—C$_6$H$_5$ | H | H | H | Cl | V/0.75 | I/9.48 | 518/520 (M + H) |
| 119 | ![morpholine-CO-N] | H | H | H | Cl | V/0.76 | I/3.10<br>II/4.055 | 498/500 (M + H) |
| 120 | Cl | H | H | CO$_2$H | Cl | V/0.21 | II/4.438 | 463/465 (M + H) |
| 121 | Cl | H | CO$_2$H | H | H | V/0.40 | II/3.925 | 429/431 (M + H) |
| 122 | ![piperazine-CH2-C6H5] | H | H | H | Cl | IV/0.90 | I/10.18 | 587/589 (M + H) |
| 123 | ![piperidine-CO-N] | H | H | H | Cl | IV/0.87 | I/6.75 | 496/498 (M + H) |
| 124 | —CO—NH—CH$_2$—CH(CH$_3$)$_2$ | H | H | H | Cl | V/0.90 | I/10.77<br>II/5.237 | 484/486 (M + H) |
| 125 | —CO$_2$H | H | H | H | Br | V/0.27 | II/4.863 | 473/475 (M + H) |
| 126 | H | F | F | H | H | V/0.51 | I/4.16 | 387 (M + H) |

TABLE 1-continued

| Ex. No. | V | W | X | Y | Z | TLC system/ $R_f$ value | HPLC system/ $R_t$ value (min.) | (+) FAB-MS m/e |
|---|---|---|---|---|---|---|---|---|
| 127 | —CO—NH—<cyclopropyl> | H | H | H | Cl | V/0.83 | I/6.02 | 468/470 (M + H) |
| 128 | <pyridyl-CH2-NH-CO-> | H | H | H | Cl | V/0.83 | I/4.53 | 519/521 (M + H) |
| 129 | —CO—N<piperidine-4-CO2—CH2—C6H5> | H | H | H | Cl | V/0.77 | I/12.62 | 630 (M + H) |
| 130 | NH2 | H | Cl | H | H | V/0.81 | I/21.48 | 586 (M + H) |
| 131 | —CO2H | H | H | H | F | V/0.36 | II/4.300 | 413 (M + H) |
| 132 | —CO2H | H | H | H | —CH3 | V/0.36 | II/4.603 | 409 (M + H) |
| 133 | —CO2CH3 | H | H | H | —CF3 | V/0.34 | II/5.104 | 463 (M + H) |
| 134 | H | Cl | H | H | —CO2H | V/0.12 | II/3.882 | 429/431 (M + H) |
| 135 | —CO2H | H | —OCH3 | H | —OCH3 | V/0.36 | I/1.12 II/3.871 | 455 (M + H) |
| 136 | —CO—N(C4H9)2 | H | H | H | Cl | V/0.81 | I/4.13 | 540/542 (M + H) |
| 137 | —CO—N(C2H5)2 | H | H | H | Cl | V/0.78 | I/6.73 | 484/486 (M + H) |
| 138 | —CO2H | H | —CO2CH3 | H | NO2 | V/0.38 | I/9.82 | 440 (M + H) |
| 139 | —CO2CH3 | H | —CO2CH3 | H | H | V/0.57 | I/3.41 | 467 (M + H) |
| 140 | H | —CO2CH3 | F | H | H | V/0.41 | II/4.475 | 467 (M + H) |
| 141 | —CO2H | H | H | H | Cl | V/0.61 | II/4.475 | 413 (M + H) |
| 142 | —CO—NH—C6H11 | H | H | H | Cl | V/0.79 | I/12.82 | 510/512 (M + H) |
| 143 | —CO—N<piperidine-4-COO—C2H6> | H | H | H | Cl | V/0.78 | I/9.64 | 568/570 (M + H) |

TABLE 1-continued

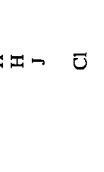

| Ex. No. | V | W | X | Y | Z | TLC system/ $R_f$ value | HPLC system/ $R_t$ value (min.) | (+) FAB-MS m/e |
|---|---|---|---|---|---|---|---|---|
| 144 | —CO—NH—CH$_2$—C(CH$_3$)$_3$ | H | H | H | Cl | V/0.81 | I/11.91 | 498/500 (M + H) |
| 145 | —COOC$_2$H$_5$ | H | H | H | Cl | V/0.80 | I/21.58 | 457/459 (M + H) |
| 146 | —COOCH$_3$ | H | OCH$_3$ | OCH$_3$ | H | V/0.57 | I/2.55 | 499 (M + H) |
| 147 | —CO$_2$H | H | C$_2$H$_5$ | H | H | V/0.53 | II/4.686 | 423 (M + H) |
| 148 | CO$_2$H | H | H | J | J | V/0.56 | II/5.471 | 647 (M + H) |
| 149 | —CO—N⟨piperazine⟩N—CHO | H | H | H | Cl | V/0.90 | II/3.729 | 525/527 (M + H) |
| 150 | —CO—N⟨piperazine⟩N—CH$_2$—CO—N⟨pyrrolidine⟩ | H | H | H | Cl | V/0.68 | I/2.84 | 608/610 (M + H) |
| 151 | —CO$_2$H | CO$_2$H | H | H | H | VI/0.34 | II/3.031 | 439 (M + H) |
| 152 | —PO(OC$_2$H$_5$)$_2$ | H | H | Cl | Cl | V/0.57 | I/20.08 | 555/557 (M + H) |
| 153 | —CO—NH—cyclopentyl | H | H | H | Cl | V/0.83 | I/11.32 | 496/498 (M + H) |
| 154 | —CO—NH—CH$_3$ | H | H | H | Cl | V/0.76 | I/3.82 | 442/444 (M + H) |
| 155 | —PO(OH)(OC$_2$H$_5$) | H | H | H | Cl | II/4.062 | II/4.473 | 527/529 (M + H) |
| 156 | NH$_2$ | H | —CO$_2$H | H | F | V/0.07 | II/3.391 | 384 (M + H) |
| 157 | —CO$_2$H | H | —CO$_2$H | H | H | V/0.41 | II/3.329 | 439 (M + H) |
| 158 | H | CO$_2$H | —OCH$_3$ | H | H | VI/0.15 | II/3.894 | 439 (M + H) |
| 159 | —CO$_2$H | H | —OCH$_3$ | —OCH$_3$ | —OCH$_3$ | VI/0.60 | | 485 (M + H) |

TABLE 1-continued

| Ex. No. | V | W | X | Y | Z | TLC system/ $R_f$ value | HPLC system/ $R_t$ value (min.) | (+) FAB-MS m/e |
|---|---|---|---|---|---|---|---|---|
| 160 | −CO−N⟨piperidine⟩−CO₂H | H | H | H | Cl | VI/0.59 | II/4.310 | 540/542 (M + H) |
| 161 | −CO₂H | H | H | H | −NH₂ | V/0.34 | I/0.75 | 410 (M + H) |

TABLE 2

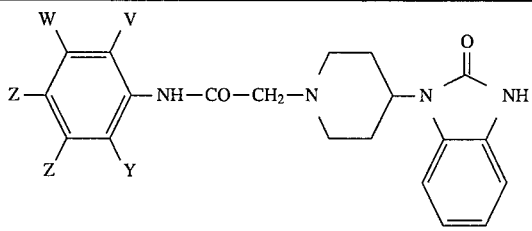

| Ex. No. | V | W | Z | Y | X | TLC system/ $R_f$ value | HPLC system/ $R_t$ value (min.) | (+) FAB-MS m/e |
|---|---|---|---|---|---|---|---|---|
| 162 | | phenyl-OH | H | H | H | | I/3.57 | 417 (M + H) |
| 163 | phenyl | | —OC$_2$H$_5$ | H | H | II/0.55 | I/6.65 | 445 (M + H) |
| 164 | | H | H$_9$C$_4$O-phenyl | H | H | II/0.50 | I/18.96 | 473 (M + H) |
| 165 | phenyl | | OC$_4$H$_9$ | H | H | II/0.57 | I/18.07 | 473 (M + H) |
| 166 | phenyl | | OC$_3$H$_7$ | H | H | II/0.41 | I/11.21 | 459 (M + H) |
| 167 | | H | phenyl | H | H | V/0.37 | II/5.071 | 445 (M + H) |

We claim:

1. A substituted (2-oxo-1-benzimidazolinyl)-piperidine of the formula (I)

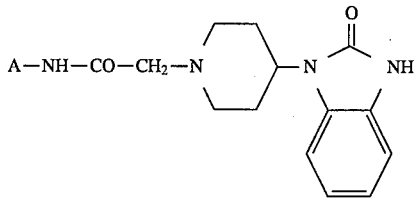

in which

A represents phenyl or naphthyl each of which is optionally substituted up to 4 times by identical or different substituents from the group consisting of halogen, carboxyl, nitro, hydroxyl, trifluoromethyl, cyano and straight-chain or branched alkyl, alkoxy, alkoxycarbonyl or alkylthio in each case having up to 8 carbon atoms, by cycloalkyl having 3 to 7 carbon atoms or by a group of the formula —P(O)(OR$^1$)(OR$^2$), —CO—R$^3$, —CO—NR$^4$R$^5$, —SO$_2$R$^6$, —NR$^7$R$^8$, —SO$_2$NR$^9$R$^{10}$, —D—R$^{11}$ OR —N=NR$^{12}$, in which R$^1$ and R$^2$ are identical or different and denote hydrogen or straight-chain or branched alkyl having up to 6 carbon atoms, R$^3$ denotes straight-chain or branched alkyl having up to 6 carbon atoms, morpholine or phenyl which is optionally substituted by halogen, R$^4$ and R$^5$ are identical or different and denote hydrogen, cycloalkyl having 3 to 7 carbon atoms, or straight-chain or branched alkyl having up to 6 carbon atoms, which is optionally substituted by phenyl, carboxyl or pyridyl, or by straight-chain or branched alkoxycarbonyl having up to 6 carbon atoms, R$^6$ denotes phenyl or straight-chain or branched alkyl having up to 6 carbon atoms, R$^7$ and R$^8$ are identical or different and denote hydrogen, phenyl, straight-chain or branched alkyl or acyl in each case having up to 6 carbon atoms, or a radical of the formula —C(S)—NR$^{15}$R$^{16}$, in which R$^{15}$ denotes hydrogen or methyl and R$^{16}$ denotes straight-chain or branched alkoxycarbonyl having up to 6 carbon atoms, $R^9$ and $R^{10}$ are identical or different and denote hydrogen, straight-chain or branched alkyl having up to 6 carbon atoms or phenyl, D denotes an oxygen or sulphur atom, $R^{11}$ and $R^{12}$ are identical or different and denote phenyl which is optionally substituted by halogen, or a salt thereof.

2. A compound or salt thereof according to claim 1, in which

A represents phenyl or naphthyl, each of which is optionally substituted up to 4 times by identical or different substituents selected from the group consisting of fluorine, chlorine, bromine, carboxyl, nitro, hydroxyl, trifluoromethyl, cyano and straight-chain or branched alkyl, alkoxy, alkoxycarbonyl or alkylthio in each case having up to 7 carbon atoms, by cyclopropyl, cyclopentyl or cyclohexyl, or by a group of the formula —P(O)—(OR$^1$)(OR$^2$), —CO—R$^3$, —CO—NR$^4$R$^5$, —SO$_2$R$^6$, —NR$^7$R$^8$, —SO$_2$NR$^9$R$^{10}$, —D—R$^{11}$ or —N=NR$^{12}$, in which $R^1$ and $R^2$ are identical or different and denote hydrogen or straight-chain or branched alkyl having up to 5 carbon atoms, $R^3$ denotes straight-chain or branched alkyl having up to 5 carbon atoms, morpholine or phenyl which is optionally substituted by fluorine, chlorine or bromine, $R^4$ and $R^5$ are identical or different and denote hydrogen, cyclopropyl, cyclopentyl, cyclohexyl or straight-chain or branched alkyl having up to 5 carbon atoms, which is optionally substituted by phenyl, carboxyl or pyridyl, or by straight-chain or branched alkoxycarbonyl having up to 5 carbon atoms, $R^6$ denotes phenyl or straight-chain or branched alkyl having up to 5 carbon atoms, $R^7$ and $R^8$ are identical or different and denote hydrogen, phenyl, straight-chain or branched alkyl or acyl in each case having up to 5 carbon atoms, or a radical of the formula —C(S)—NR$^{15}$R$^{16}$, in which $R^{15}$ denotes hydrogen or methyl and $R^{16}$ denotes straight-chain or branched alkoxycarbonyl having up to 5 carbon atoms, $R^9$ and $R^{10}$ are identical or different and denote hydrogen, straight-chain or branched alkyl having up to 5 carbon atoms or phenyl, D denotes an oxygen or sulphur atom, $R^{11}$ and $R^{12}$ are identical or different and denote phenyl which is optionally substituted by fluorine, chlorine or bromine.

3. A compound or salt thereof according to claim 1, in which

A represents phenyl or naphthyl, each of which is optionally substituted up to 4 times by identical or different substituents selected from the group consisting of fluorine, chlorine, bromine, iodine, carboxyl, nitro, hydroxyl, trifluoromethyl, cyano and straight-chain or branched alkyl, alkoxy, alkoxycarbonyl or alkylthio in each case having up to 6 carbon atoms, by cyclopropyl, cyclopentyl or cyclohexyl, or by a group of the formula —P(O)—(OR$^1$)(OR$^2$), —CO—R$^3$, —CO—NR$^4$R$^5$, —SO$_2$R$^6$, —NR$^7$ R$^8$, —SO$_2$NR$^9$R$^{10}$, —D—R$^{11}$, or —N=NR$^{12}$, in which $R^1$ and $R^2$ are identical or different and denote hydrogen or straight-chain or branched alkyl having up to 4 carbon atoms, $R^3$ denotes straight-chain or branched alkyl having up to 4 carbon atoms, morpholine or phenyl which is optionally substituted by fluorine, chlorine or bromine, $R^4$ and $R^5$ are identical or different and denote hydrogen, phenyl, cyclopropyl, cyclopentyl, cyclohexyl or straight-chain or branched alkyl having up to 5 carbon atoms, which is optionally substituted by phenyl, carboxyl or pyridyl, or by straight-chain or branched alkoxycarbonyl having up to 4 carbon atoms, $R^6$ denotes phenyl or straight-chain or branched alkyl having up to 4 carbon atoms, $R^7$ and $R^8$ are identical or different and denote hydrogen, phenyl, straight-chain or branched alkyl or acyl in each case having up to 4 carbon atoms, or a radical of the formula —C(S)—NR$^{15}$R$^{16}$, in which $R^{15}$ denotes hydrogen or methyl and $R^{16}$ denotes straight-chain or branched alkoxycarbonyl having up to 4 carbon atoms, $R^9$ and $R^{10}$ are identical or different and denote hydrogen, straight chain or branched alkyl having up to 4 carbon atoms or phenyl, D denotes an oxygen or sulphur atoms, and $R^{11}$ and $R^{12}$ are identical or different and denote phenyl which is optionally substituted by fluorine, chlorine or bromine.

4. Process for the preparation of a compound of the formula (I), according to claim 1, which comprises reacting a compound of the formula (II)

A—NH—CO—CH$_2$—L    (II)

in which

L is a leaving group, with 4-(2-oxo-1-benzimidazolinyl)-piperidine of the formula (III)

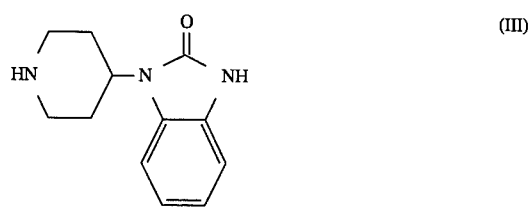

(III)

in an inert solvent in the presence of potassium carbonate and sodium iodide.

5. A compound according to claim 1, wherein such compound is 1-[2-(2-carboxy-4-chlorophenyl)amino-2-oxo-ethyl]-4-(2-oxo- 1-benzimidazolinyl)piperidine of the formula

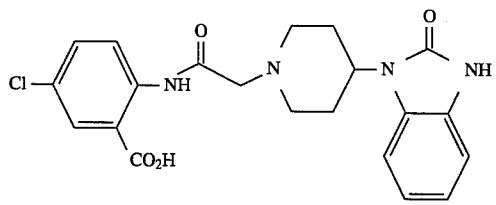

or a salt thereof.

6. A compound according to claim 1, wherein such compound is 1-[2-(2,4-difluorophenyl)amino- 2-oxo-ethyl-]4-(2-oxo-1-benzimidazolinyl)piperdine of the formula

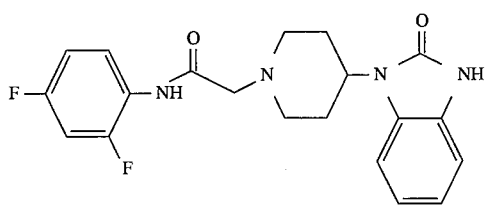

or salt thereof.

7. A compound according to claim 1, wherein such compound is 1-[2-(2-aminophenyl)amino-2-oxoethyl]-4-(2-oxo-1-benzimidazolinyl)piperdine of the formula

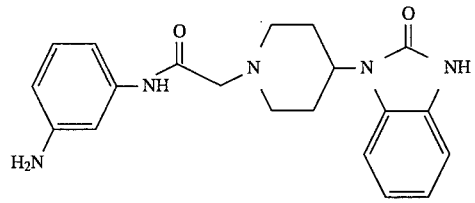

or salt thereof.

8. A compound according to claim 1, wherein such compound is 1-[2-(4-amino-2-chlorophenyl)amino-2-oxoethyl]-4-(2-oxo-1-benzimidazolinyl)piperidine of the formula

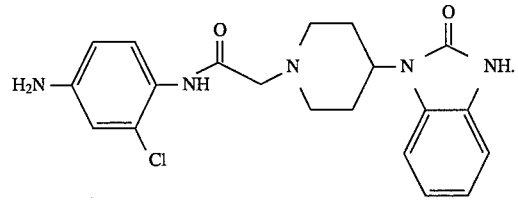

9. A compound according to claim 1, wherein such compound is

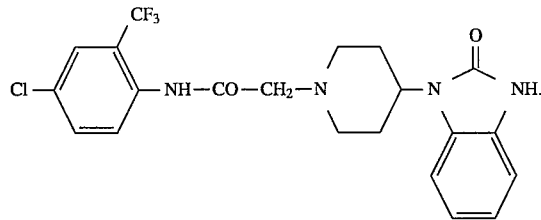

or salt thereof.

10. A compound according to claim 1, wherein such compound is

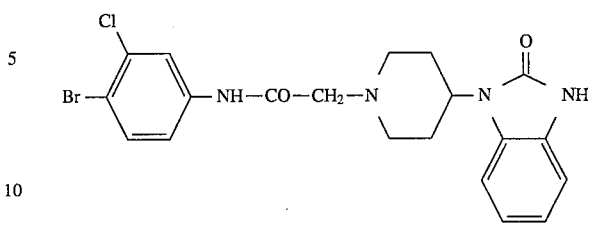

or salt thereof.

11. A compound according to claim 1, wherein such compound is

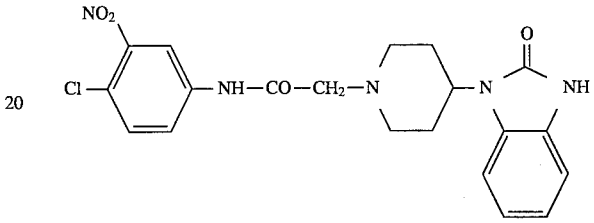

or salt thereof.

12. A compound according to claim 1, wherein such compound is

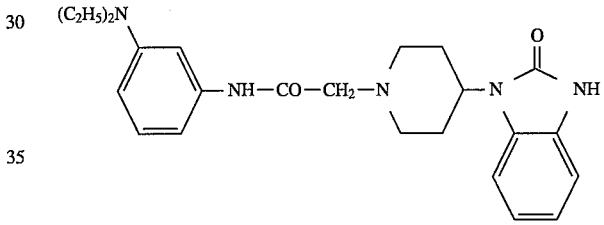

or salt thereof.

13. A compound according to claim 1, wherein such compound is

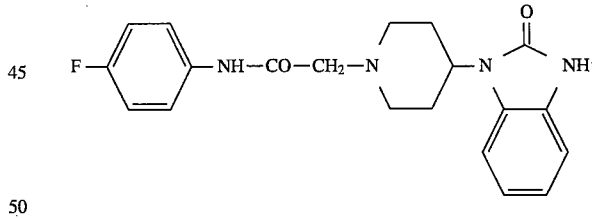

or salt thereof.

* * * * *

UNITED STATES PATENT AND TRADEMARK OFFICE
CERTIFICATE OF CORRECTION

PATENT NO. : 5,571,921
DATED : November 5, 1996
INVENTOR(S) : Bender, et al.

It is certified that error appears in the above-indentified patent and that said Letters Patent is hereby corrected as shown below:

Title Page & Col 1    Delete " PEPERIDINES " and substitute
line 3                -- PIPERIDINES --

Signed and Sealed this

Twenty-fifth Day of March, 1997

Attest:

BRUCE LEHMAN

*Attesting Officer*    *Commissioner of Patents and Trademarks*